(12) United States Patent
Scott

(10) Patent No.: US 11,259,913 B2
(45) Date of Patent: Mar. 1, 2022

(54) BREAST IMPLANT WITH POSITION MARKER

(71) Applicant: Susan Scott, Merritt Island, FL (US)

(72) Inventor: Susan Scott, Merritt Island, FL (US)

( * ) Notice: Subject to any disclaimer, the term of this patent is extended or adjusted under 35 U.S.C. 154(b) by 115 days.

(21) Appl. No.: 16/782,448

(22) Filed: Feb. 5, 2020

(65) Prior Publication Data
US 2020/0246132 A1 Aug. 6, 2020

Related U.S. Application Data

(60) Provisional application No. 62/801,812, filed on Feb. 6, 2019.

(51) Int. Cl.
*A61F 2/12* (2006.01)

(52) U.S. Cl.
CPC ........ *A61F 2/12* (2013.01); *A61F 2250/0098* (2013.01)

(58) Field of Classification Search
CPC .......................................................... A61F 2/12
USPC ......................................................... 623/7–8
See application file for complete search history.

(56) References Cited

U.S. PATENT DOCUMENTS

| | | |
|---|---|---|
| 4,795,463 A | 1/1989 | Gerow |
| 4,863,470 A | 9/1989 | Carter |
| 5,409,004 A | 4/1995 | Sloan |
| 6,203,570 B1 | 3/2001 | Baeke |
| 6,363,940 B1 | 4/2002 | Krag |
| 7,736,391 B2 | 6/2010 | Schwibner et al. |
| 9,113,844 B2 | 8/2015 | Hollstien |
| 9,636,210 B2 | 5/2017 | Hristov et al. |
| 9,750,600 B2 | 9/2017 | Mayo Martin |
| 9,839,507 B2 | 12/2017 | Harms et al. |
| 9,949,821 B2 | 4/2018 | Beeckler |
| 9,980,809 B2 | 5/2018 | Lebovic et al. |
| 10,176,412 B2 | 1/2019 | Geissler et al. |
| 10,258,460 B2 | 4/2019 | Moses et al. |
| 2004/0254438 A1* | 12/2004 | Chuck ...................... A61F 2/14 600/398 |
| 2006/0229721 A1* | 10/2006 | Ku ........................... A61F 2/12 623/8 |
| 2009/0024225 A1 | 1/2009 | Stubbs |
| 2010/0137999 A1 | 6/2010 | Shohat |
| 2011/0098576 A1* | 4/2011 | Hollstien ............. A61B 5/4851 600/476 |
| 2012/0302874 A1* | 11/2012 | Hollstien ............. A61B 5/4851 600/424 |
| 2013/0226296 A1 | 8/2013 | Chernomorsky et al. |
| 2014/0200396 A1* | 7/2014 | Lashinski ................. A61F 2/12 600/37 |
| 2017/0296273 A9* | 10/2017 | Brown ................... A61B 34/10 |
| 2017/0367809 A1* | 12/2017 | Glicksman ................ A61F 2/02 |
| 2018/0064530 A1 | 3/2018 | Glicksman |
| 2018/0200020 A1 | 7/2018 | Hermann et al. |
| 2018/0353739 A1 | 12/2018 | Grinstaff et al. |

(Continued)

*Primary Examiner* — Suzette J Gherbi
(74) *Attorney, Agent, or Firm* — Dunlap Bennett & Ludwig, PLLC

(57) ABSTRACT

A breast implant includes an outer shell made of a polymer and a filler material disposed within the outer shell. At least one opaque marking is disposed on the outer shell. The opaque marker is visible through the skin when a light emitter emits light through the chest tissue. This allows a user to determine if the breast implant is flipped or rotated based on the location of the opaque marker.

10 Claims, 2 Drawing Sheets

(56) References Cited

U.S. PATENT DOCUMENTS

| | | |
|---|---|---|
| 2019/0117379 A1 | 4/2019 | Quiros et al. |
| 2019/0142574 A1* | 5/2019 | Quiros .................... A61L 27/50 623/8 |
| 2019/0240052 A1* | 8/2019 | Chen ..................... A61F 5/0046 |
| 2020/0085526 A1* | 3/2020 | Schuessler ................ A61F 2/12 |
| 2020/0129258 A1* | 4/2020 | Feinberg ........... A61M 39/0208 |
| 2020/0352704 A1* | 11/2020 | Schuessler ................ A61F 2/12 |
| 2021/0169504 A1* | 6/2021 | Brown ................. A61B 6/4441 |

* cited by examiner

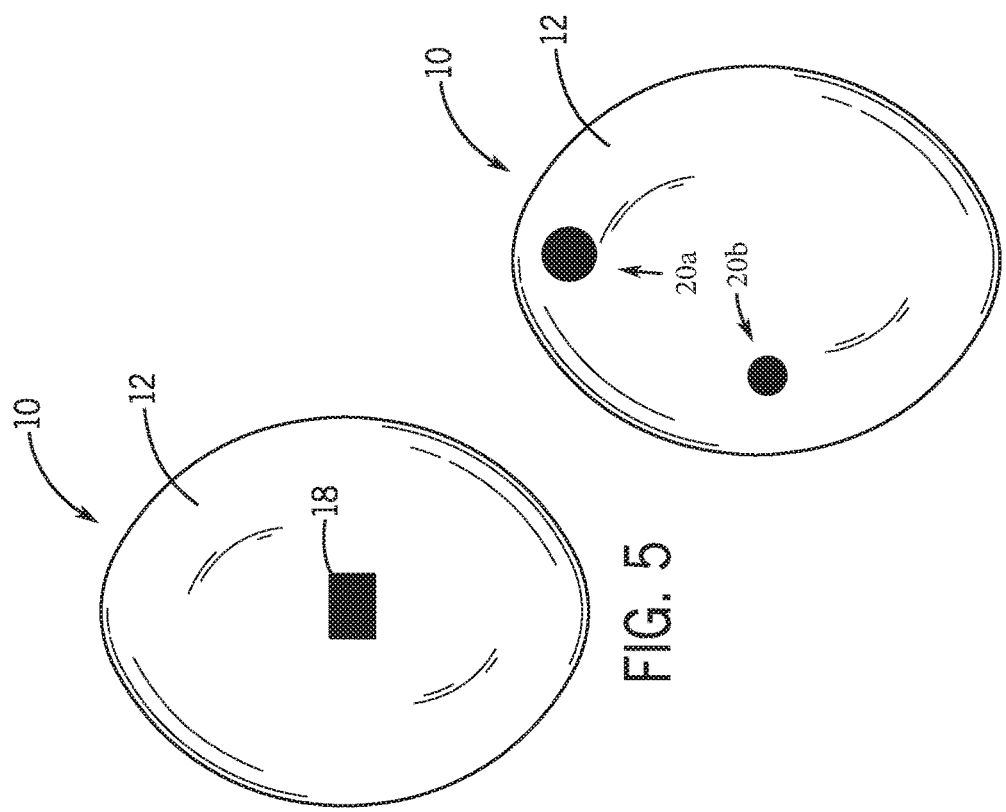
FIG. 3
FIG. 4
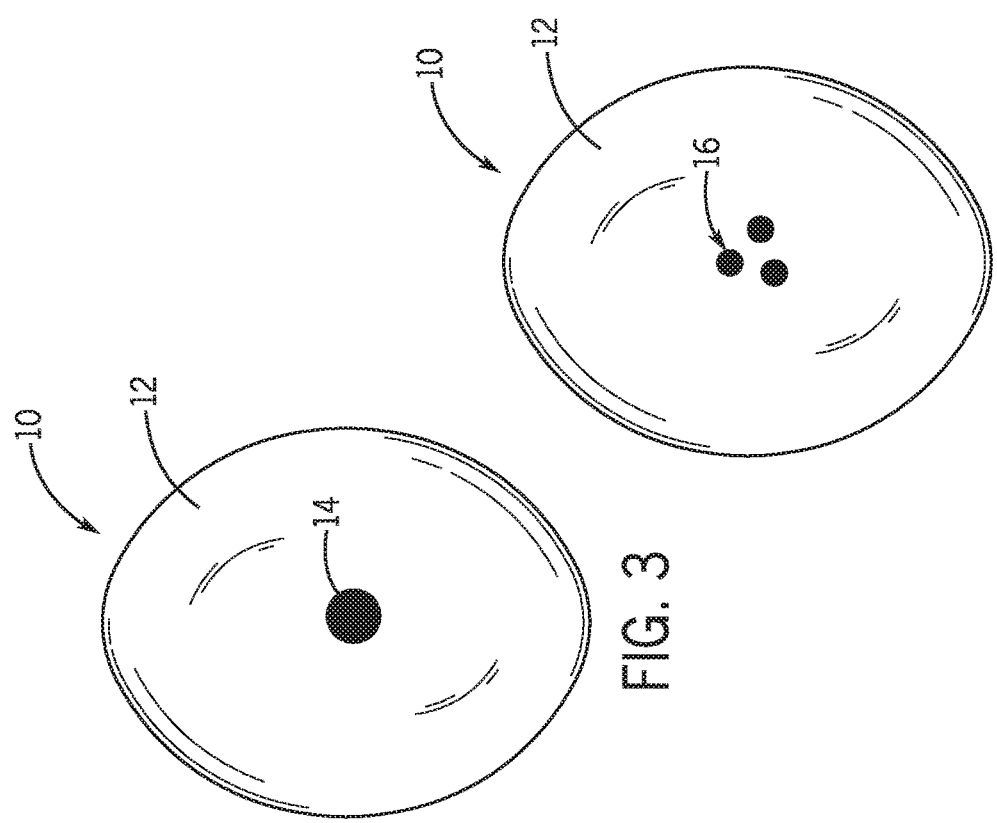
FIG. 5
FIG. 6

BREAST IMPLANT WITH POSITION MARKER

CROSS-REFERENCE TO RELATED APPLICATION

This application claims the benefit of priority of U.S. provisional application No. 62/801,812, filed Feb. 6, 2019, the contents of which are herein incorporated by reference.

BACKGROUND OF THE INVENTION

The present invention relates to breast implants and, more particularly, to a breast implant with a position marker.

Mastectomy is the medical term for the surgical removal of one or both breasts. A mastectomy is usually carried out to treat breast cancer. In some cases, people believed to be at high risk of breast cancer have the operation as a preventive measure.

A breast implant is a prosthesis used to change the size, shape, and contour of a person's breast. In reconstructive plastic surgery, breast implants can be placed to restore a natural looking breast following a mastectomy or to correct congenital defects and deformities of the chest wall. The implant is placed either under or over the pectoralis major muscle.

Mastectomies require removal of all breast tissue. For women who have had mastectomies, breast implants tend to move around underneath the chest skin because of the absence of breast tissue. For example, a woman who sleeps on their side or stomach may experience breast implants rotating or flipping overnight. When a breast implant rotates or flips, it may not readily be apparent to the individual. Because nerves are cut during a mastectomy there is no sensation to alert a woman of implant malposition.

As can be seen, there is a need for a system and method of detecting when a breast implant has rotated or flipped.

SUMMARY OF THE INVENTION

In one aspect of the present invention, a breast implant comprises: an outer shell made of a polymer; and a filler material disposed within the outer shell, wherein at least one opaque marking is disposed on the outer shell.

In another aspect of the present invention, a method of determining if a breast implant is displaced comprises steps of: implanting a breast implant underneath the chest skin of a human body, the breast implant comprising: an outer shell made of a polymer, and a filler material disposed within the outer shell, wherein at least one opaque marking is disposed on the outer shell; and placing a light emitter against the chest skin of the human body, wherein at least one opaque marking is visible through the chest skin when light from the light emitter is shining through the chest skin, and a location of at least one opaque marking indicates if the breast implant is displaced within the human body.

These and other features, aspects and advantages of the present invention will become better understood with reference to the following drawings, description and claims.

BRIEF DESCRIPTION OF THE DRAWINGS

FIG. 3 is a front view of an embodiment of the present invention;

FIG. 4 is a front view of an embodiment of the present invention;

FIG. 5 is a front view of an embodiment of the present invention; and

FIG. 6 is a front view of an embodiment of the present invention.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Figure 2:
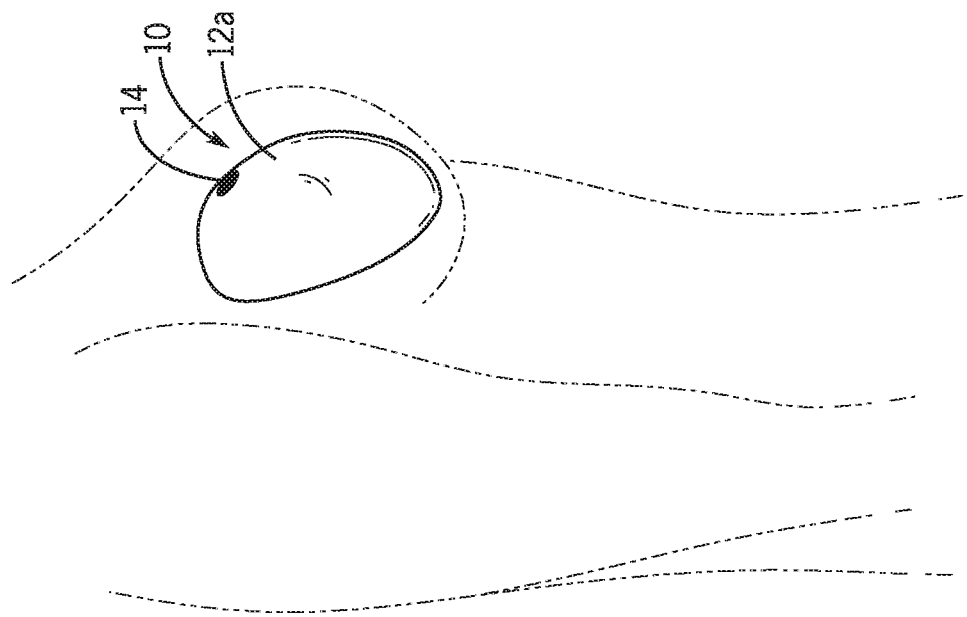
FIG. 2 is a side perspective view of an embodiment of the present invention, shown in use and in an undesired orientation.
Figure 1:
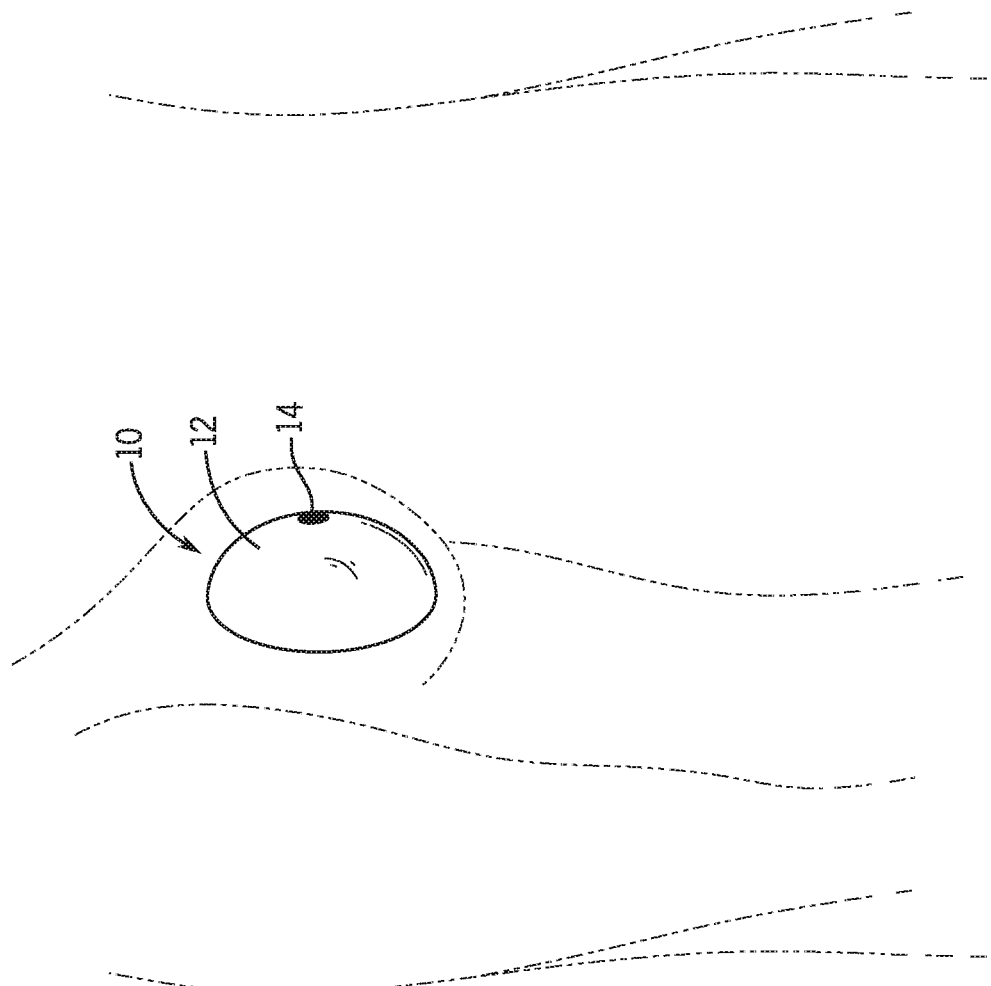
FIG. 1 is a side perspective view of an embodiment of the present invention, shown in use and in a desired orientation.

Referring to FIGS. 1 through 6, the present invention includes a breast implant. The breast implant includes an outer shell 10 made of a polymer and a filler material 12 disposed within the outer shell 10. At least one opaque marking 14 is disposed on the outer shell 10. The opaque marker 14 is visible through the skin when a light emitter emits light through the chest tissue. This allows a user to determine if the breast implant is flipped or rotated based on the location of the opaque marker 14.

As mentioned above, the breast implant includes an outer shell 10 and a filler material 12 disposed within the outer shell 10. The outer shell may be made of an elastomer silicone or any material that may be used as an outer shell for a breast implant. The filler material 12 may be a saline solution, a viscous silicone gel, or any filler that may be used as a filler material for a breast implant. The outer shell 10 may include a flat rear surface and a rounded front surface. For example, the outer shell 10 may include a tear drop shape or a dome shape.

The opaque marking 14 of the present invention may be printed on an outer surface of the breast implant. The opaque marking 14 is a dark color and allows little or no light to pass through. For example, the opaque marking 14 may be black, brown, or other dark color. As illustrated in FIGS. 3 through 5, the opaque marking 14 may be disposed at a central portion of the rounded front surface. The opaque marking 14 may be circular, square 18, dotted 16, or other shape or pattern. The opaque marking 14 being disposed at a central portion of the rounded front surface allows a user to determine if the breast implant has flipped from front to back.

As illustrated in FIG. 6, the present invention may include a first opaque marking 20a and a second opaque marking 20b. The first opaque marking 20a may be distinguishable from the second opaque marking 20b. For example, the first opaque marking 20a may be larger than the second opaque marking 20b. Alternatively, the first opaque marking 20a and the second opaque marking 20b may be a different shape or pattern. The first opaque marking 20a may be disposed at a first position of a periphery of the rounded front surface and the second opaque marking 20b may be disposed at a second position of a periphery of the rounded front surface.

Since the first opaque marking 20a and the second opaque marking 20b are distinguishable and located at different positions along the periphery of the rounded front surface, a user may determine if the breast implant has rotated along an x-axis, y-axis, z-axis, or a combination thereof. For example, the first opaque marking 20a may be located at a twelve o'clock position on the rounded front surface and the second opaque marking 20b may be located at a nine o'clock position on the rounded front surface. Alternatively, the first opaque marking 20a and the second opaque marking 20b may be located at different positions along the periphery. This allows a user to observe whether the breast implant has flipped on its side, flipped from top to bottom, or rotated clockwise or counterclockwise.

A method of determining if a breast implant is displaced may include steps of: implanting a breast implant underneath a chest skin of a human body, the breast implant having: an outer shell made of a polymer, and a filler material disposed within the outer shell, wherein at least one opaque marking is disposed on the outer shell; and placing a light emitter against the chest skin of the human body. Then at least one opaque marking is visible through the chest skin when light from the light emitter is shining through the chest skin, especially in an area with low or little light. A location of the at least one opaque marking indicates if the breast implant is displaced within the human body. As for the example in FIG. 6, the first opaque marking 20a is located at a twelve o'clock position on the rounded front surface and the second opaque marking 20b is located at a nine o'clock position on the rounded front surface when the breast implant is in a correct position within the human body. When the first opaque marking 20a and the second opaque marking 20b are displaced from the above-mentioned position, the breast implant is displaced and needs to be repositioned.

It should be understood, of course, that the foregoing relates to exemplary embodiments of the invention and that modifications may be made without departing from the spirit and scope of the invention as set forth in the following claims.

What is claimed is:

1. A breast implant comprising:
   an outer shell made of a polymer, wherein the outer shell comprises a flat rear surface and a rounded front surface;
   a filler material disposed within the outer shell;
   a first opaque marking disposed at a first position of a periphery of the rounded front surface; and
   a second opaque marking disposed at a second position of a periphery of the rounded front surface.

2. The breast implant of claim 1, wherein the outer shell is an elastomer silicone shell.

3. The breast implant of claim 2, wherein the filler material comprises one of a saline solution and a viscous silicone gel.

4. The breast implant of claim 1, wherein the first opaque marking is distinguished from the second opaque marking.

5. The breast implant of claim 4, wherein the first opaque marking is located at a twelve o'clock position on the rounded front surface and the second opaque marking is located at a nine o'clock position on the rounded front surface.

6. A method of determining if a breast implant is displaced comprising steps of:
   implanting a breast implant underneath the chest skin of a human body, the breast implant comprising: an outer shell made of a polymer, wherein the outer shell comprises a flat rear surface and a rounded front surface, and a filler material disposed within the outer shell, wherein a first opaque marking is disposed at a first position of a periphery of the rounded front surface and a second opaque marking is disposed at a second position of a periphery of the rounded front surface; and
   placing a light emitter against the chest skin of the human body, wherein
   each opaque marking is visible through the chest skin when light from the light emitter is shining through the chest skin, and
   a location of the at least one opaque marking indicates if the breast implant is displaced within the human body.

7. The method of claim 6, wherein the outer shell is an elastomer silicone shell.

8. The method of claim 7, wherein the filler material comprises one of a saline solution and a viscous silicone gel.

9. The method of claim 6, wherein the first opaque marking is distinguished from the second opaque marking.

10. The method of claim 9, wherein the first opaque marking is located at a twelve o'clock position on the rounded front surface and the second opaque marking is located at a nine o'clock position on the rounded front surface when the breast implant is in a correct position within the human body.

* * * * *